United States Patent [19]

Barnett et al.

[11] Patent Number: 4,628,138
[45] Date of Patent: Dec. 9, 1986

[54] CATALYST AND PROCESS FOR OLIGOMERIZATION OF ETHYLENE

[75] Inventors: Kenneth W. Barnett, Worthington; Mary J. Brown, Columbus, both of Ohio

[73] Assignee: Ashland Oil, Inc., Columbus, Ohio

[21] Appl. No.: 778,143

[22] Filed: Sep. 20, 1985

[51] Int. Cl.$^4$ .............................................. C07C 2/02
[52] U.S. Cl. .................................... 585/531; 585/510; 585/511; 585/520; 585/533
[58] Field of Search ................ 585/510, 511, 520, 531, 585/533

[56] References Cited

U.S. PATENT DOCUMENTS

| | | |
|---|---|---|
| 3,134,824 | 5/1964 | Walker . |
| 3,424,816 | 1/1969 | McClure et al. ..................... 585/531 |
| 3,459,826 | 8/1969 | Barnett et al. ....................... 585/531 |
| 3,532,765 | 10/1970 | Barnett . |
| 4,024,202 | 5/1977 | Burnham ............................. 585/520 |
| 4,272,406 | 6/1981 | Beach . |
| 4,272,407 | 6/1981 | Beach . |
| 4,293,725 | 10/1981 | Beach . |

OTHER PUBLICATIONS

"The Kinetics of Ethylene Polymerization in Nickel-Y Zeolite" Author: Lothar Riekert; Journal of Catalysis 19, 8–11 (1970).

*Primary Examiner*—Curtis R. Davis
*Attorney, Agent, or Firm*—Wood, Herron & Evans

[57] ABSTRACT

An improved heterogeneous catalyst effective to catalyze the oligomerization of ethylene is formed by hydrogenating bis($\eta^5$-cyclopentadienyl) nickel (nickelocene) onto an omega zeolite support in the presence of a small, but effective amount of a promoter. The promoters are oxides of nickel, iron or copper and mixtures thereof. The catalyst is particularly effective in terms of selectivity and reactivity in catalyzing the formation of 1-butene from ethylene.

15 Claims, No Drawings

CATALYST AND PROCESS FOR OLIGOMERIZATION OF ETHYLENE

BACKGROUND OF THE INVENTION

1. Field of Invention

The present invention relates to the oligomerization of olefins with a supported nickel catalyst, particularly a promoted nickel-zeolite catalyst.

More particularly, the present invention relates to the formation of 1-butene by reacting ethylene in the presence of this nickel-zeolite catalyst.

The present invention further relates to a novel heterogeneous nickel-zeolite catalyst.

2. Description of the Prior Art

A variety of oligomerization catalysts are currently known. These include both homogeneous and heterogeneous catalysts. In particular nickel compounds have been used to catalyze the oligomerization of lower olefins to olefinic products of higher molecular weight, e.g., dimmers, trimers, tetramers or the like.

The selectivity towards particular products and the overall reactivity depend to a large extent upon the catalyst used as well as reaction conditions. Barnett U.S. Pat. No. 3,532,765 discloses an ethylene oligomerization process using cyclopentenyl(cyclopentadienyl) nickel supported on an inorganic oxide support. This catalyst exhibits a relatively low reactivity. Barnett U.S. Pat. No. 3,134,824 discloses bis (cyclopentadienyl) nickel deposited on a support such as silica, alumina, titania, zirconia, thoria, boria, and mixtures thereof. This catalyst exhibits a relatively low selectivity for 1-butene and an overall low reactivity.

Walker, et al, U.S. Pat. No. 3,134,824, describe a process using nickelocene [bis ($\eta^5$-cyclopentadienyl) nickel] supported on silica-alumina as a catalyst for oligomerization of olefins. However, this catalyst is not selective nor is it active at temperatures below one hundred degrees Centigrade.

Other catalysts are disclosed in Beach et al U.S. Pat. Nos. 4,272,406, 4,272,407 and 4,293,725. The patents disclose tris(cyclopentadienyl) trinickel dicarbonyl catalysts. These catalysts exhibit a relatively low selectivity toward 1-butene relative to other C-4 compounds specifically in the range of 11–44% 1-butene, and further produce considerable quantities of higher molecular weight oligomers, e.g., hexenes, octenes, etc.

A nickel II salt derived from phosphinoacetate is currently used as a homogeneous catalyst for oligomerization of olefins. This produces a relatively high proportion of higher molecular weight olefins. In fact the product distribution of $C_6$–$C_{20}$ olefins is relatively flat.

Triethylaluminum is also used as an oligomerization catalyst. The product distribution of $C_4$–$C_8$ and higher olefins is weighted towards lower molecular weight olefins.

A particularly desirable product is 1-butene. It can be used in the formation of poly 1-butene a very useful polymer. However, the known oligomerization catalysts are unsuitable for production of a very high concentration of 1-butene from ethylene.

SUMMARY OF THE INVENTION

The present invention is premised upon the realization that a catalyst, formed by depositing nickel by reduction of nickelocene in the presence of a promoter onto an omega zeolite support, acts to catalyze the oligomerization of ethylene to form 1-butene with extremely high selectivity towards 1-butene. Further the catalyst of the present invention is very reactive under mild conditions. Accordingly, it provides a catalyst uniquely suited for the production of 1-butene from ethylene.

DETAILED DESCRIPTION OF THE INVENTION

According to the present invention ethylene is reacted in the presence of a catalyst to form 1-butene. The catalyst is a heterogeneous catalyst formed from a bis ($\eta^5$-cyclopentadienyl) nickel compound also referred to as nickelocene or a nickelocene derivative, reduced onto an omega zeolite support in the presence of a promoter which is an oxide of nickel, iron or copper.

Catalyst Formation

The omega type zeolite support is a synthetic crystalline zeolite the production of which is described in U.S. Pat. No. 4,241,036 which is incorporated herein by reference. Omega zeolites are readily prepared by digesting and crystallizing an aqueous mixture having an overall composition expressed in terms of mole ratios of oxides falling within the following range:

$$\frac{Na_2O + ((CH_3)_4N)_2O}{SiO_2} \text{ from about 0.1 to about 0.6}$$

$$\frac{((CH_3)_4N)_2O}{((CH_3)_4N)_2O + Na_2O} \text{ from about greater than 0 to about 0.6}$$

$$\frac{SiO_2}{Al_2O_3} \text{ from about 5 to about 30}$$

$$\frac{H_2O}{((CH_3)_4N)_2O + Na_2O} \text{ from about 10 to about 125}$$

A particularly preferred set of initial reacting compositions for producing the omega zeolites again expressed in terms of mole ratios is as follows:

$$\frac{Na_2O + ((CH_3)_4N)_2O}{SiO_2} \text{ from about 0.2 to about 0.4}$$

$$\frac{((CH_3)_4N)_2O}{((CH_3)_4N)_2O + Na_2O} \text{ from about greater than 0 to about 0.2}$$

$$\frac{SiO_2}{Al_2O_3} \text{ from about 6 to about 10}$$

$$\frac{H_2O}{((CH_3)_4N)_2O + Na_2O} \text{ from about 15 to about 60}$$

Representative reactants are silica gel, silicic acid, colloidal silica, alkali metal silicate and reactive amorphous solid silicas as a source of silicon and activated alumina, gamma alumina, alumina trihydrate or alkali metal aluminate as the source of aluminum. Sodium hydroxide and tetramethylammonium hydroxide or halide are typical convenient sources of sodium and tetramethyl ammonium ions. Preferred sources of silica are the reactive solid silicas which include materials known commercially as Hi-Sil, Cab-O-Sil, Zeosyl, QUSO, Arc silica and the aqueous colloidal silica sols which include such materials as Nalcoag, Ludox, Syton and Mertone.

The reaction system is formed by placing all the required reactants in the proportions hereinbefore defined in a reaction vessel and bringing the temperature of the system to a temperature of between 20° C. and 210° C., preferably between 80° C. and about 210° C. An initial aging of the reaction system at ambient temperature can be utilized if desired. Products of the highest purity have been obtained using temperatures of from about 90° C. to about 180° C. and are therefore preferred. Crystallization periods of from about 1-8 days at 80°-100° C. have been found satisfactory.

After the reaction period the zeolite crystals are filtered off. The mass of zeolite crystals is washed preferably with distilled water and conveniently on the filter, until the effluent wash water in equilibrium with the zeolite has a pH of between 9 and 12. Thereafter the crystals are dried, conveniently in a vented oven, at a temperature of between 25° C. and 150° C.

Preferred omega zeolites are obtained from Linde Division of Union Carbide and are referred to as ELZ-omega-5 zeolite and ELZ-omega-6 zeolite. As used herein and in the claims the ELZ-omega-5 zeolite refer to a zeolite, also called a molecular seive, having the following chemical and physical properties.

| (a) Chemical composition anhydrous basis | |
|---|---|
| $Al_2O_3$ | 16.3 wt percent |
| $SiO_2$ | 75.7 wt percent |
| $Na_2O$ | 6.5 wt percent |
| $SiO_2/Al_2O_3$ | molar ratio 7.7 |
| $Na_2O/Al_2O_3$ | molar ratio 0.6 |
| (b) Physical properties | |
| Form - powder | |
| Unit cell constants $a_o$ | 18.20 angstroms |
| Unit cell constants $c_o$ | 7.59 angstroms |
| Free aperture 12 ring, | 7.5 angstroms |
| Largest molecule absorbed | $(C_4F_9)_3N$ |
| Effect of dehydration | Stable to 750° Centigrade |
| Surface area (1 pt. BET) 240 | square meters/grams |
| $O_2$ capacity (at −183° C., 100 torr) | 15.0% |

Surface area (1 pt. BET) 240 square meters/grams
$O_2$ capacity (at −183° C., 100 torr) 15.0% As used herein and in the claims ELZ-omega-6 zeolite refers to a zeolite also called a molecular seive having the following chemical and physical properties.

| (a) Chemical Composition Anhydrous Basis | |
|---|---|
| $Al_2O_3$ | 18.8 wt percent |
| $SiO_2$ | 78.9 wt percent |
| $Na_2O$ | 0.68 wt percent |
| $SiO_2/Al_2O_3$ | 7.1 molar ratio |
| $Na_2O/Al_2O_3$ | 0.06 molar ratio |
| (b) Physical Properties | |
| Form - powder | |
| Unit cell constants $a_o$ | 18.20 angstroms |
| Unit cell constants $c_o$ | 7.57 angstroms |
| Surface area (1 pt. BET) | 300 square meters/grams |
| $O_2$ capacity (at −183° C., 100 torr) | 15.8% |

The catalyst is formed in the presence of a promoter. The promoter used in the formation of the catalyst is an oxide of nickel, iron or copper. Preferred oxides are nickel oxide (NiO), ferric oxide ($Fe_2O_3$) and cupric oxide (CuO) as well as mixtures of these.

The nickelocene compound used in the present invention is bis($R_a$-$\eta^5$ cyclopentadienyl) nickel or ($R_a$-$\eta^5$ cyclopentadienyl) ($\eta^5$ cyclopentadienyl) nickel wherein R represents one or more $C_1$-$C_{10}$ alkyl groups and wherein R is specifically substituted onto one or both of the cyclopentadienyls and "a" represents 0-5 and preferably 0 or 1. Specific compounds include methyl nickelocene $(CH_3C_5H_4)(C_5H_5)Ni$, 1,1'-dimethyl nickelocene $(CH_3C_5H_4)_2Ni$, ethyl nickelocene $(C_2H_5C_5H_4)(C_5H_5)Ni$ and so on. Preferably unsubstituted nickelocene is used which can be purchased in a commercial grade such as that sold by Strem Chemical Co. Hereinafter substituted and unsubstituted nickelocene as defined above will be generally referred to as the nickelocene compound.

Formation of Catalyst

The catalyst is formed by reducing the nickelocene compound in the presence of the promoter onto the omega zeolite support. Care must be taken to insure no water is present because the nickelocene compound as well as the formed catalyst are very reactive with water and can be easily deactivated.

In the reaction it is preferable to use from 0.1 to 10 weight percent of the nickelocene compound based on weight of omega zeolite and from 2 to 50 weight percent of promoter based on the weight of the nickelocene compound.

The reaction is conducted in the presence of an inert diluent preferably an aliphatic hydrocarbon in a pressurized autoclave. Suitable organic diluents are those which can be easily removed from the product mixture and recycled such as heptane, decane, decalin, etc. The ratio of diluent to catalyst can be from 50 parts by weight to 15 parts by weight.

Preferably the reduction is performed by hydrogenation. The reaction is conducted by flushing the reactor with nitrogen, charging the reactor with the nickelocene compound, promoter, zeolite and diluent, purging the reactor first with nitrogen and then with hydrogen and charging the reactor with hydrogen to a pressure of from about 300 to about 900 pounds per square inch (20.7-62.1 bars) for a period of from about 30 to about 90 minutes. Preferably the pressure is maintained at about 500 psi. While pressurized the contents of the autoclave are heated to at least about 80° C. to about 150° C., and preferably at about 100° C. for 20 minutes to about an hour.

The color of the contents of the reactor can indicate if the reaction forming the catalyst has been completed. The solution of nickelocene compound has a bright green color. Upon reduction by hydrogen the solution becomes clear. Therefore if the contents of the autoclave are clear, the reaction is complete.

Oligomerization Reaction

Because the catalyst is so sensitive to moisture it is preferred to use the catalyst in situ to eliminate the need for transferring the catalyst from one reactor to another. Accordingly, to use the catalyst in an oligomerization reaction, unused hydrogen is vented off and the catalyst composition resulting from the reaction is used in the inert diluent.

The oligomerization reaction can be conducted in a batch or continuous reactor. In this reaction, ethylene is reacted with itself at elevated pressure with agitation to form preferably 1-butene. The reaction is exothermic accordingly cooling is required.

The ethylene, supplied as a gas, is charged into the reactor to increase the reactor pressure as desired. The ethylene can be in the form of reagent grade ethylene or alternately may be contained in low concentration as the byproduct of various petroleum distillation processes and may contain other olefins such as proplyene. In order to prevent deactivation of the catalyst, water must be removed from the ethylene source prior to being contacted with the catalyst. Further in order to prevent hydrogenation of ethylene, hydrogen should be removed from the ethylene source.

The reaction temperature should be preferably about room temperature generally from about 20° to 70° C. Higher temperatures cause the equilibrium to shift towards formation of 2-butene as opposed to 1-butene. This is particularly so when the reaction temperature exceeds about 40° C. Further at higher temperatures higher molecular weight olefins such as $C_6$ and $C_8$ olefins are produced in higher quantities. Preferably the temperature should be from about 25° to about 40° C.

The amount of catalyst present relative to the amount of ethylene converted is relatively low. Generally about 4,000 moles of ethylene can be converted per mole of nickel per hour. Including the support this corresponds to 17 grams of product per gram of catalyst per hour. In this respect it was determined that the loading of the nickel onto the zeolite support increases the activity of the catalyst if a higher level of promoter is used. Optimum composition of the catalyst in the present form is about 1-5% of the nickelocene compound and 0.1-0.5% promoter (preferably nickel oxide promoter) and the remainder support.

The reaction is conducted in the liquid phase for about 1 to about 60 minutes. The reaction pressure can be from about 150 pounds per square inch to about 1,000 pounds per square inch (10.3 to 68.9 bars). The preferred range is from about 400 to about 500 psi (27.6 to 34.5 bars). Preferably the reaction time will be maintained at from about 5 to about 20 minutes.

EXAMPLES

In the following examples the catalyst is prepared by first flushing a 300 milliliter autoclave with nitrogen gas. The autoclave is equipped with a stirrer and cooling coils. Under a blanket of nitrogen, 6.0 grams zeolite support, 0.4 grams of commercial grade nickelocene, 90 mls of heptane solvent and the designated promoter are charged into the 300 milliliter autoclave under the nitrogen blanket. The reactor is then closed, flushed with nitrogen, flushed with hydrogen, and finally pressurized with hydrogen. The mixture is hydrogenated at 100° C., 500 psig for one hour and the hydrogen is subsequently vented after cooling.

The oligomerization reaction was conducted by flushing the reactor with ethylene and subsequently adding ethylene to the designated pressure. Table I shows the results obtained following this procedure. The maximum temperature of the oligomerization reaction, the time of the oligomerization reaction, ethylene pressure are all provided. Further, the particular support is also provided Ω-6 designating omega 6 zeolite and Ω-5 designating omega 5 zeolite. The amount and promoter added is also designated.

To facilitate analysis of the product the gas phase was vented and the liquid product mixture is analyzed by gas chromatography.

Table I

TABLE I

| Ex No. | Max. Temp. | Time | Ethylene Pressure PSIG | Support | Weight Milligrams Promoter | Butene Wt. Grams | Hexenes Wt. Grams | Octenes Wt. Grams | Percent 1-Butene in $C_4^=$s |
|---|---|---|---|---|---|---|---|---|---|
| 1 | 36 | 1 hr. | 390 | Ω-6 | 20 mg - NiO | 40.5 | 20.7 | 44 | 20.7 |
| 2 | 42 | 1.25 hr. | 500 | Ω-6 | 20 mg - $Fe_2O_3$ | 52.2 | 18.5 | 2.3 | 40 |
| 3 | 40 | 1 hr. | 500 | Ω-6 | 50 mg CuO | 43.9 | 13.7 | 1.0 | 45 |
| 4 | 81 | 1 hr. | 500 | Ω-6 | 40 mg - NiO | 61.4 | 35.8 | 8.9 | 25 |
| 5 | 35 | 1 hr. | 500 | Ω-5 | 20 mg - NiO | 17.5 | 2.3 | trace | 84 |

To demonstrate the effect on varying the amount of promoter and nickelocene in the catalyst the above Examples were repeated wherein the weight relative proportion of support, nickelocene and promoter were varied. The reaction conditions for formation of the catalyst were the same as those stated in Examples 1-5. The support in each of these experiments was omega-6 zeolite and the promoter was nickel oxide. The results are shown in Table II.

TABLE II

| Ex No. | Max. Temp. | Time Minutes | Grams Support | Grams $Cp_2Ni$ | Grams NiO | Grams Product | Selectivity Butenes | Selectivity Hexenes | Selectivity Octenes | Percent 1-Butene in $C_4^=$s |
|---|---|---|---|---|---|---|---|---|---|---|
| 6 | 36 | 60 | 6.0 | 0.4 | 0.04 | 68.5 | 82 | 16 | 2 | 60 |
| 7 | 46 | 60 | 6.0 | 0.4 | 0.02 | 70.2 | 82 | 16 | 2 | 61 |
| 8 | 35 | 60 | 6.0 | 6.4 | 0.01 | 18.1 | 91 | 9 | — | 84 |
| 9 | 85 | 20 | 6.0 | 0.8 | 0.04 | 97.8 | 58 | 33 | 9 | 39 |
| 10 | 36 | 60 | 3.0 | 0.2 | 0.02 | 36.5 | 88 | 11 | 1 | 74 |

$Cp_2Ni$ = Nickelocene

Comparative Examples

The following comparative examples illustrate how the catalyst compositions of the present invention are effective relative to other catalysts. All catalysts were again prepared according to the method described with respect to Examples 1-5 in a 300 milliliter autoclave with 6.0 grams of support using 0.4 grams of nickelocene. The results are shown in Table III.

Table III

TABLE III

| | Temp. °C. | Press. psig | Grams $C_4$ | Grams $C_6$ | Grams $C_8$ | 1-$C_4$= % | Remarks |
|---|---|---|---|---|---|---|---|
| Ex. 11 | 21 | 500 | — | — | — | — | Silicalite, 20 mg NiO |
| Ex. 12 | 30 | 500 | 2.5 | tr | — | — | LZY-82, 20 mg NiO |

TABLE III-continued

|  | Temp. °C. | Press. psig | Grams $C_4$ | Grams $C_6$ | Grams $C_8$ | 1-$C_4$= % | Remarks |
|---|---|---|---|---|---|---|---|
| Ex. 13 | 28 | 500 | — | — | — | — | LZY-52, 20 mg NiO |
| Ex. 14 | 28 | 500 | 1.1 | tr | — | — | Omega-6, 10 mg NiO |

In Examples 11-13 different zeolite type supports were used. Example 11 shows the use of silicalite, Example 12 LZY-82 zeolite, and Example 13 LZY-52 zeolite. Again catalysts formed with these supports were ineffective. Example 14 shows the effect of using too low a concentration of promoter with the nickelocene. In this example only ten milligrams of nickel oxide was used per 0.4 grams of nickelocene.

The present invention can also be conducted using a continuous reactor wherein the catalyst is in an extruded form, held in a wire mesh basket. In such a reactor the ethylene which may be provided at low concentrations such as in the off-gas of petroleum processing, is injected into the high pressure reactor containing the solvent such as decane, the catalyst and a stirrer. Cooling may also be provided. A portion of the produced oligomers are retained in the solvent and and the remainder of the product and the unreacted gases are vented off the top. The reaction can be stopped periodically and the oligomer/solvent solution removed. Alternately, the oligomer/solvent can be continuously drained from the reactor and new solvent added. In this process, the catalyst is the same with the exception that the catalyst may include a binder such as silica to facilitate the formation of pellitized catalysts. Further the catalyst may be retained in a powder form and simply removed with the formed oligomer, separated and returned to the reaction vessel.

The reaction can also be conducted in the vapor phase by passing fuel gas containing about 20% ethylene in an inert carrier over the dry catalyst. The ethylene is preferably diluted with nitrogen.

Although the invention has been described with reference to specific details of certain illustrative embodiments, it is not intended that it shall be limited thereby except insofar as such details appear in the following claims.

We claim:

1. A method of oligomerizing an olefin comprising: contacting said olefin with a nickel-omega zeolite catalyst at a pressure, temperature and for a time effective to cause oligomerization of said olefin; said catalyst comprising
   a nickelocene compound reduced onto an omega zeolite support in the presence an effective amount of a promoter;
   wherein the nickelocene compound is selected from the group consisting of ($R_a$-$\eta^5$ cyclopentadienyl) (cyclopentadienyl) Ni and bis($R_a$-$\eta^5$ cyclopentadienyl) Ni wherein R represents $C_1$-$C_{10}$ alkyl and "a" represents 0-5; and
   wherein the promoter is selected from the group consisting of an oxide of copper, nickel, iron and mixtures thereof.

2. The method claimed in claim 1 wherein said olefin is selected from the group consisting of ethylene and mixtures of ethylene and propylene.

3. The method claimed in claim 2 wherein the weight percentage of the nickelocene compound based on the weight of omega zeolite is from about 0.1 to about 10 weight percent.

4. The method claimed in claim 3 wherein the weight percent of promoter based on the weight of the nickelocene compound ranges from about 2 to about 50 weight percent.

5. The method claimed in claim 2 wherein said the nickelocene compound is reduced onto said omega zeolite by hydrogenation.

6. The method claimed in claim 4 wherein said promoter is selected from the group consisting of ferric oxide, cubric oxide, nickel oxide and mixtures thereof.

7. The method claimed in claim 2 wherein said nickelocene compound is bis($\eta^5$cyclopentadienyl)Ni.

8. The method claimed in claim 7 wherein said pressure effective to cause oligomerization is from about 150 pounds per square inch to about 1,000 pounds per square inch.

9. The method claimed in claim 8 wherein said temperature effective to cause oligomerization is from about 20° to about 70° C.

10. The method claimed in claim 9 wherein said time effective to cause oligomerization is from about 1 to about 60 minutes.

11. The method claimed in claim 9 wherein said temperature effective to cause oligomerization is from about 25° to about 40° C.

12. The method claimed in claim 10 wherein said time effective to cause olifomerization is from about 5 to about 20 minutes.

13. The method claimed in claim 2 wherein said zeolite has the following general chemical composition

| (a) Chemical composition anhydrous basis | |
|---|---|
| $Al_2O_3$ | 16.3 wt percent |
| $SiO_2$ | 75.7 wt percent |
| $Na_2O$ | 6.5 wt percent |
| $SiO_2/Al_2O_3$ | molar ratio 7.7 |
| $Na_2O/Al_2O_3$ | molar ratio 0.6 |

14. The method claimed in claim 2 wherein said zeolite has the following general chemical composition

| (a) Chemical Composition Anhydrous Basis | |
|---|---|
| $Al_2O_3$ | 18.8 wt percent |
| $SiO_2$ | 78.9 wt percent |
| $Na_2O$ | 0.68 wt percent |
| $SiO_2/Al_2O_3$ | 7.1 molar ratio |
| $Na_2O/Al_2O_3$ | 0.06 molar ratio |

15. The method claimed in claim 1 wherein said olefin is reacted in the presence of an inert diluent.

* * * * *